Figure 1:
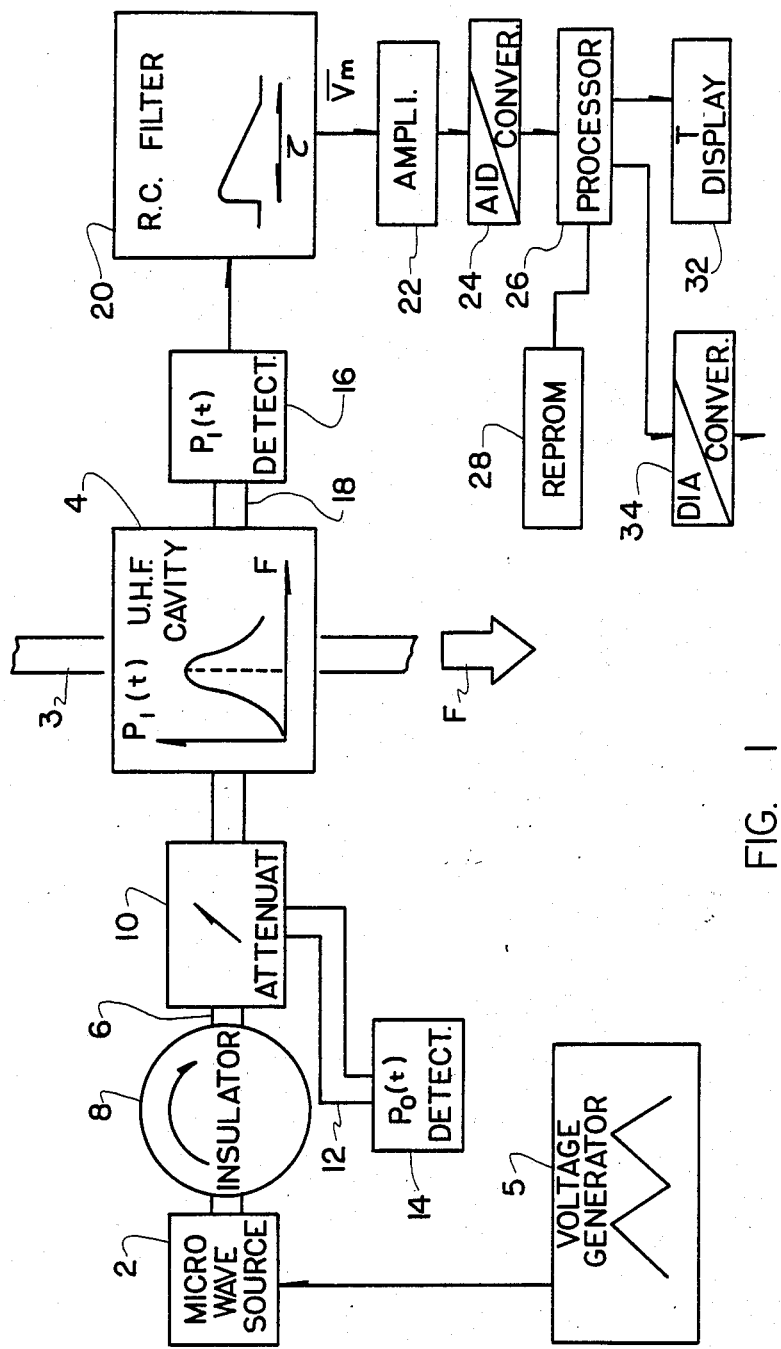

United States Patent [19]

Lacombe et al.

[11] Patent Number: 4,885,527
[45] Date of Patent: Dec. 5, 1989

[54] DEVICE FOR CONTINUOUSLY MEASURING THE RATE AT WHICH FIBERS CONDUCTING OR NOT CONDUCTING ELECTRICITY ARE IMPREGNATED BY A SUBSTANCE

[75] Inventors: Jean F. Lacombe, Saint Medard En Jalles; Jean L. Miane, Talence, both of France

[73] Assignee: Aerospatiale Societe Nationale Industrielle, Paris, France

[21] Appl. No.: 225,541

[22] Filed: Jul. 28, 1988

[30] Foreign Application Priority Data

Aug. 4, 1987 [FR] France ................... 87 11059

[51] Int. Cl.$^4$ .................................... G01N 22/04
[52] U.S. Cl. ..................... 324/58.5 C; 324/58 C; 73/160
[58] Field of Search ............ 324/58 R, 58.5 R, 58 C, 324/58.5 C; 73/159, 160

[56] References Cited

U.S. PATENT DOCUMENTS

| | | | |
|---|---|---|---|
| 4,060,762 | 11/1977 | McKeown | 324/58 C |
| 4,297,874 | 11/1981 | Sasaki | 324/58.5 C |
| 4,350,883 | 9/1982 | Lagarde | 324/58 C |
| 4,581,575 | 4/1986 | Osaki | 324/58.5 C |

FOREIGN PATENT DOCUMENTS

| | | |
|---|---|---|
| 0011185 | 5/1980 | European Pat. Off. . |
| 2942971 | 5/1981 | Fed. Rep. of Germany ..... 324/58.5 C |
| 2386033 | 10/1978 | France . |
| 2529340 | 12/1983 | France . |
| 2556470 | 6/1985 | France . |
| 0074449 | 6/1980 | Japan ................... 324/58.5 C |
| 0053455 | 3/1988 | Japan ................... 324/58.5 C |

OTHER PUBLICATIONS

Tiuri: "Microwave Method for Measurement of Fiber Orientation in Paper"-MW Conference-Sep. 1974.

*Primary Examiner*—Reinhard J. Eisenzopf
*Assistant Examiner*—Jose M. Solis
*Attorney, Agent, or Firm*—Pearne, Gordon, McCoy & Granger

[57] ABSTRACT

Device for the continuous measurement of the impregnation level by a substance of fibers which may or may not conduct electricity. This device has a cylindrical resonant cavity (2) excited in accordance with mode $TE_{113}$ and provided with first microwave input and output (e1, s1) for respective coupling to a microwave source (2) and a detector (16) of the microwave power from the cavity when the fiber is conductive, so that the first component $(\overline{E1})$ of the electrical field of the resonant mode is perpendicular to the fiber, second microwave input and output (e2, s2) for respective coupling to the source and the detector when the fiber is nonconductive, so that the second component $(\overline{E2})$ of the electric field of the resonant mode is parallel to the fiber, a mode filter (40) for eliminating from the cavity the first component of the electric field when the fiber is non-conductive, and means for processing the signal supplied by the detector in order to deduce the impregnation rate therefrom.

9 Claims, 5 Drawing Sheets

DEVICE FOR CONTINUOUSLY MEASURING THE RATE AT WHICH FIBERS CONDUCTING OR NOT CONDUCTING ELECTRICITY ARE IMPREGNATED BY A SUBSTANCE

DESCRIPTION

The present invention relates to a device for the continuous measurement of the rate of impregnation, by a sufficiently viscous substance, of fibers which may or may not be electricity conducting using an ultra-high frequency cavity.

It more particularly applied in the field of the production of composite materials formed from e.g. metal or carbon conductive fibers or glass, Kevlar, silica or alumina non-conductive fibers, impregnated by resins (polyester, epoxy, etc.) hardened by polymerization and/or crosslinking. These composite materials are used for producing parts (aircraft, shuttles).

In the field of composite materials, frequent use is made of fibers and wires which can be in the form of thin, narrow strips or films, which must be impregnated by a polymerizable resin, the nature of which is dependent on the envisaged application.

The impregnation rate varies from 20 to 40, as a function of the intended use, this rate being defined by the ratio of the resin mass, for a given fiber length, to the total mass of the impregnated fiber. For a particular application, the impregnation rate must be accurately determined and must stay within tolerances which are as close as possible and also constant from one end of the fiber to the other.

FR-A-2 556 470 describes a process and a device for continuously measuring the impregnation rate by resin of conductive fibers and using an ultra-high frequency cavity. The basic measuring principle is based on the disturbances to a microwave resonant cavity due to the introduction into said cavity of a conductive fiber.

To this end, the measuring process consists of passing the resin-impregnated conductive fiber through the ultra-high frequency cavity in a direction orthogonal to the microwave electric field in the cavity and continuously measuring the microwave power variations at the cavity outlet. These variations are within a certain measuring range proportional to the resin impregnation rate of the fiber.

The process and device illustrated in the aforementioned specifications suffer from the disadvantage of being very specific and only suitable for measurements on conductive fibers. Using the same fixed equipment, they do not permit "mixed" measurements, i.e. either on electricity conducting, or electricity non-conducting fibers.

Moreover, the microwave source has in the long term thermal variations which are prejudicial to the measurement. Thus, the frequency variations of the microwave source lead to variations in the power transmitted by the cavity and which are independent of the properties of the impregnated fiber to be checked. In other words, the frequency variation of the source introduces variations into the measurement of the impregnation rate and therefore measurement errors.

Moreover, in a field differing from that of the invention, EP-A-0 011 185 discloses an apparatus for measuring the water content of non-electrically conducting isotropic substances also utilizing the measurement of disturbances of a microwave resonant cavity. The cavity used has a rectangular section. The measurement is carried out on samples passing through the microwave cavity in a direction parallel to that of the microwave electric field therein. These samples are of powders, granules, pastes or liquids, which does not permit a continuous measurement in situ, i.e. directed at the place of manufacture of the materials from which the samples have been taken.

Moreover, the resonant cavity operates in different resonant modes are a function of the measurement to be performed of the type $TE_{01n}$ (with n being a positive interger), so that to each mode corresponds a measuring frequency and a measurable moisture range.

This device for measuring the moisture or humidity of non-conductive samples advantageously has means for stabilizing the frequency of the microwave source avoiding a drift in the measurements over a period of time.

Unfortunately, this device does not make it possible to measure conductive materials. Thus, in a resonant cavity with a rectangular section, there is no component of the resonant electric field of the cavity which is oriented perpendicular to the sample to be analyzed. Thus, the resonant cavity always works with an electric field oriented parallel to the sample.

Moreover, the use of a resonant cavity with a rectangular section has a low quality factor limiting the sensitivity of the measuring device.

The present invention relates to a device making it possible to continuously measure the rate at which fibers can be impregnated by a substance, whereby said fibers may or may not conduct electricity and which can be used on an industrial scale. In particular, said device is able to accurately measure on conducting on non-conducting fibers while retaining the same mechanical positioning with respect to the continuous passage of the fibers in the ultra-high frequency cavity. Moreover, this device makes it possible to overcome the frequency drift of the microwave source, while improving the stability of the measuring signal.

More specifically, the present invention relates to a device for the continuous measurement of the impregnation rate, by any substance of a fiber having a microwave source, a resonant cavity which can be coupled to the microwave source via a first waveguide, the cavity having an axis of symmetry parallel to a first direction (x) and a passage for the fiber, traversing the cavity in its centre and oriented parallel to a second direction (y) perpendicular to the first direction, a detector of the microwave power transmitted by the cavity and which can be coupled to the latter via a second waveguide and transforming said power into an electric signal, means for processing the electric signal in order to deduce therefrom the impregnation rate and means for displaying the impregnation rate, characterized in that the cavity has a circular section excited in accordance with a resonant mode $TE_{11n}$, with n being an uneven number exceeding 1 and having (a) a first input and a first output for microwaves, oriented parallel to a third direction (z) perpendicular to the first and second directions (x, y), said first input and output being respectively connected to the first and second guides when the fiber is conductive, so that the first component ($\vec{E1}$) of the electric field of the resonant mode $TE_{11n}$, oriented in the third direction, is perpendicular to the conductive fiber, (b) a second input and a second output for microwaves, oriented parallel to the second direction, said second input and output being respectively connected to the first and second guides when the fiber in non-conductive, so that the second component ($\vec{E2}$) of the electric field of the resonant mode $TE_{11n}$, oriented in the second direction, is parallel to the non-coonductive fiber and (c) a mode filter for eliminating from the resonant cavity said first component ($\vec{E1}$) of the electric field when the fiber is non-conductive.

This device makes it possible to control the impregnated fiber production process, more particularly by controlling the impregnation rate of the fibers, while ensuring a real time tracking of the quality control of the composite material formed from said fibers.

The use of a cylindrical cavity according to the invention, its operation on a single resonant mode $TE_{11n}$, its double system of microwave inputs and outputs, as well as the use of the mode filter make it possible to retain the same mechanical positioning of the fiber and cavity for continuous measurements on electricity conducting or non-conducting fibers.

In the case of resonant modes $TE_{11n}$ of a cavity with a circular section, a same input simultaneously excites two resonant modes $TE_{11n}$ having different polarizations or components designated $\vec{E1}$ and $\vec{E2}$, which is not possible with a cavity having a rectangular section. However, the coupling between the incident exciting wave and the polarizations $\vec{E1}$ and $\vec{E2}$ is not the same.

The use of two separate microwave inputs and, in parallel, two separate outputs makes it possible to retain a correct coupling in accordance with the polarization used during the measurement of the impregnation rate.

A further advantage of a cylindrical cavity compared with a rectangular cavity is a higher quality factor, so that the measuring device has a better sensitivity.

The inventive use of a mode filter has the effect of eliminating the undesirable polarization $\vec{E2}$ during the measurement of the impregnation rate of a non-conductive fiber.

In order that the mode filter is effective, it must be made from a metal having a maximum electrical conductivity and is in particular made from cooper, silver or gold, or optionally some other metal coated with a gold or silver deposit a few micrometers thick.

Its shape must be that of a rigid wire of maximum fineness having a diameter between 0.5 and 1 mm in order to retain a certain mechanical strength or rigidity, penetrating the microwave cavity. This conductive wire is positioned in accordance with one of the diameters of the resonant cavity and is oriented perpendicular to the first component $\vec{E1}$ of the electric field which it is wished to retain, or parallel to the third direction. Moreover, it must be located at a maximum of the electric field of the resonant mode, i.e. for a mode $TE_{113}$ at 1/6 of the length of the cavity, on one or other side of the passage intended for the fibers. Advantageously, the penetration of the mode filter into the cavity is approximately the same as the radius of the cavity, although this is not critical.

According to the invention, the ultra-high frequency cavity is made from metal. In order that said cavity has a maximum quality factor, the latter is either formed from a solid block of a good electricity conducting metal (brass, copper) or from a block made from any metal, whereby the inner walls of said block are then coated with a highly conductive polished film of gold or silver. The resonant cavity operates on a single mode $TE_{11n}$ with n being either 3, 5, 7 or 9, preferably 3.

In order to avoid frequency drifts of the microwave source and therefore measuring errors, frequency stabilization means for the microwave source are provided. These means can e.g. be constituted by a frequency closed-loop control having a reference loop connected to an automatic control chain for the frequency of the source, in order to control the control voltage of said source, the reference loop incorporating a reference cavity and a reference detector. However, this solution is heavy, because it requires a second reference cavity, associated with a second detection system.

Another solution consists of using a function generator supplying a sawtooth voltage leading to a modulation of the frequency of the source about the resonant frequency of the disturbed cavity over a frequency range which must be as large as possible compared with the mid-height width of the peak of the resonance curve giving the variations of the microwave power transmitted by the disturbed cavity as a function of the exciting frequency thereof.

The microwave power detector is in particular a microwave "contact" diode or a Schottky diode. Due to the frequency modulation of the microwave source according to the invention, the electric signal from the detector must firstly be processed by an electronic circuit converting said signal into a mean continuous signal. When said electronic circuit is a filter, the mean continuous signal obtained P2(t) is the correlation of the power transmitted at resonance by the disturbed cavity, designated P1(t), by the filtering function F(t).

A peak detector amplifier can be used in place of the filter and in this case the mean continuous signal P2(t) obtained is proportional to the signal P1(t).

The use of a sawtooth voltage generator ensures that there is no longer any disturbance by the frequency drift of the microwave source and the association with said generator of an electronic circuit converting the signal emitted by the detector into a mean continuous signal makes it possible to improve the stability of the measuring signal, because each measurement transmitted to the processing system is already a mean value of the detected signal.

This mean continuous signal is then amplified by an amplifier, followed by conversion into a digital signal by an analog-digital converter before being processed by a microprocessor, in order to transform the digital signal from the converter into a value of the impregnation rate of the conductive or non-conductive fiber.

The device according to the invention is applicable to any type of fiber, whereby the latter can be in the form of a cylindrical wire, braid, film, strip, etc. However, in the case of conductive fibers, a better stability is obtained when they are in the form of a film or strip.

Other features and advantages of the invention can be gathered from the following non-limitative description of embodiments with reference to the attached drawings, wherein show:

FIG. 1 a block diagram of a measuring device according to the invention.

Figure 2:
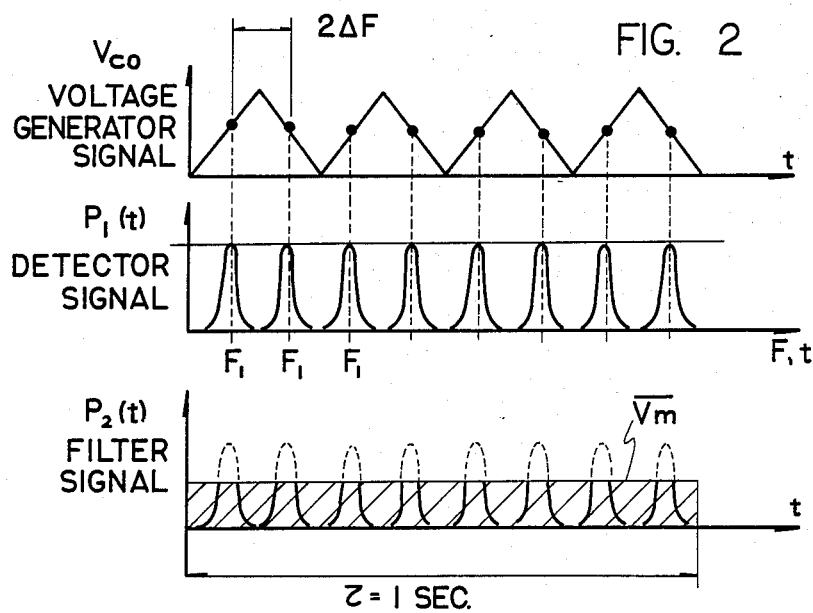

FIG. 2 the shape or path of the signals respectively from the voltage source, the detector and the electric circuit converting the detector signal into a mean continuous signal as a function of time.

Figure 3:
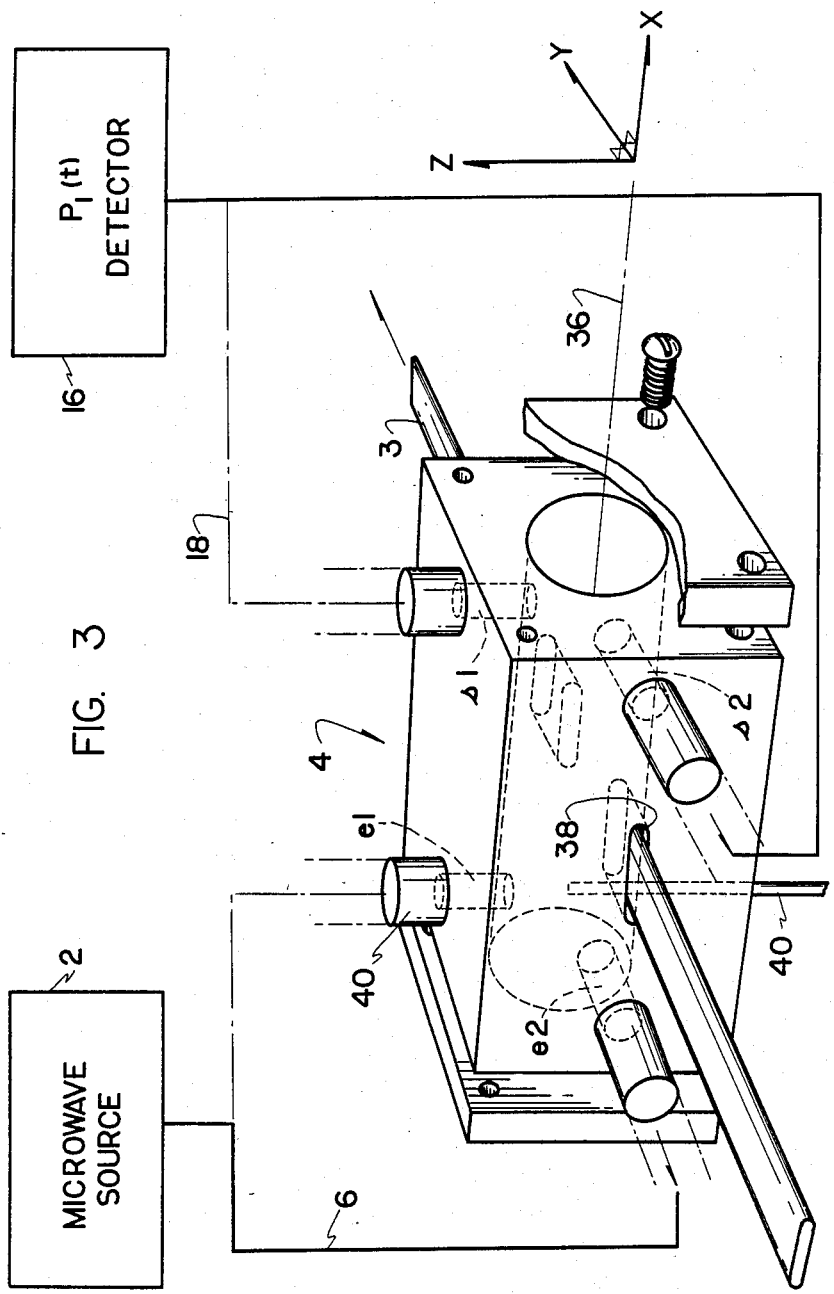
Figure 4B:
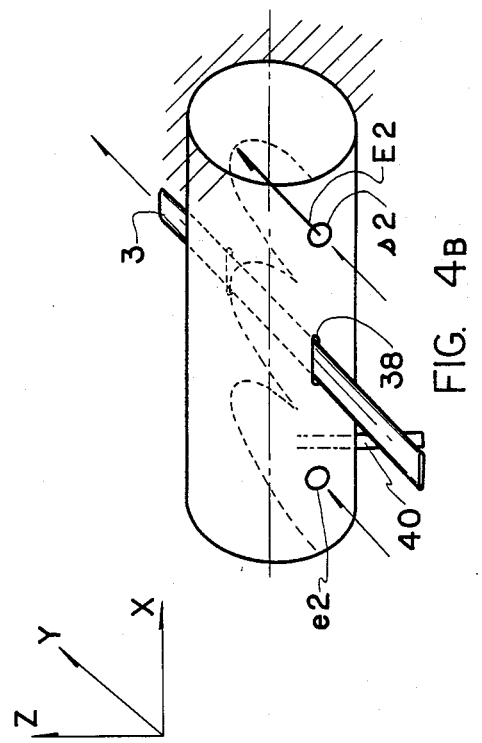
Figure 4D:
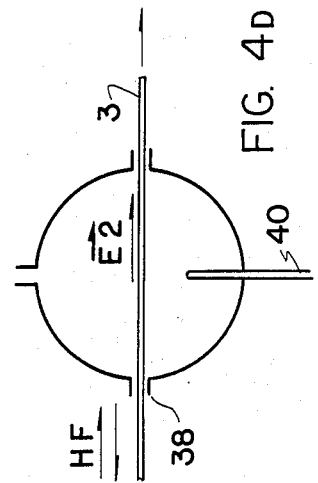
Figure 4A:
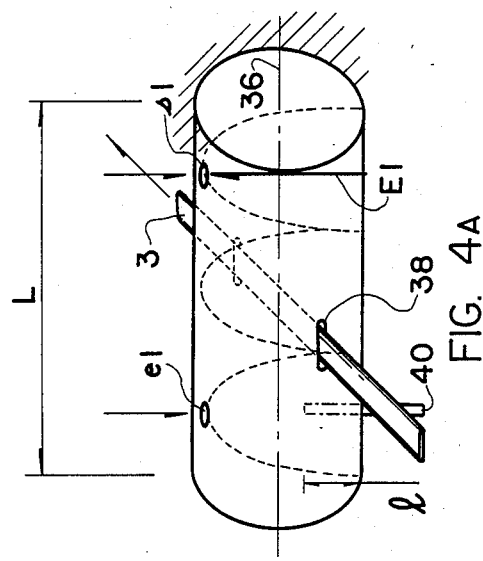
Figure 4C:
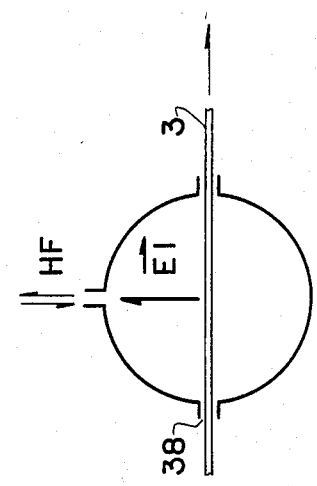

FIG. 3 diagrammatically an embodiment of the microwave cavity of the device of FIG. 1.

FIG. 4 a diagram illustrating the distribution and arrangement of the microwave electric field in the cavity of FIG. 3.

Figure 5:
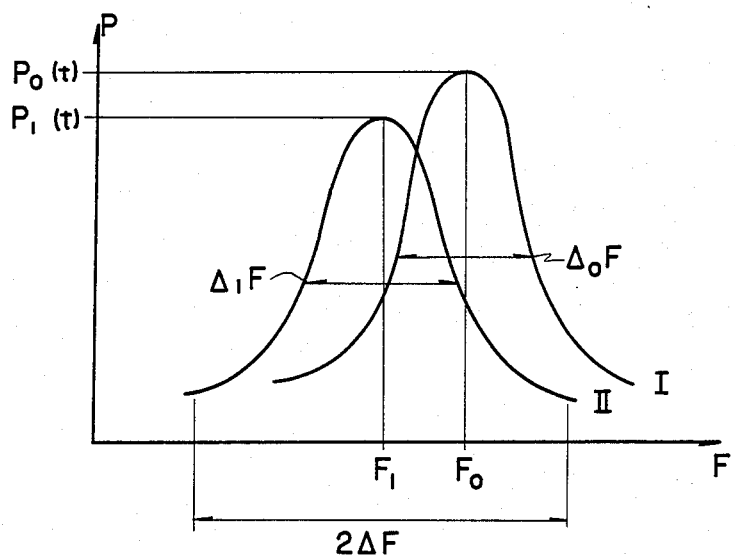

FIG. 5 Resonance curves of the microwave cavity of FIG. 3, curve I corresponding to the resonance of the empty cavity and curve II to the resonance of the cavity disturbed by an impregnated fiber.

With reference to FIG. 1, the measuring device according to the invention has a microwave source 2 constituted by a Gunn diode or a field effect transistor (FET) producing ultra-high frequency waves, whereof the frequency can be modified with the aid of a varactor. The microwaves used have in particular a frequency of 8 to 12 GHz, corresponding to the X band.

The frequency of the waves produced by source 2 is close to the resonant frequency of the ultra-high frequency cavity 4 in which continuously circulates an electricity conducting or non-conducting fiber 3, preimpregnated with a polymerizable resin. Arrow f indicates the passage direction of the fiber in the cavity.

According to the invention, the voltage supply of source 2 is provided by a generator 5 supplying a sawtooth voltage Vco, like that shown in FIG. 2, leading to a frequency modulation of the microwave source 2. This modulation consists of a frequency scan on a range $\Delta 2F$ of about ten megahertz, about the resonant cavity F1 of the disturbed resonant cavity 4. This makes it possible to ensure a frequency stabilization of source 2 and consequently ensures the stability of the measurement.

The microwaves are transferred between source 2 and ultra-high frequency cavity 4 by a flexible waveguide 6, e.g. constituted by a coaxial cable. Waveguide 6 is provided with a commercially available microwave insulator 8, which prevents any disturbance to the microwaves produced by source 2 through external electromagnetic waves.

Moreover, waveguide 6 is provided with a variable attenuator 10 making it possible to regulate the incident power Po(t) of the microwaves produced by source 2. To this end, the known attenuator 10 is connected by a coaxial conductor 12 to a detector 14 of the incident power Po(t), e.g. formed by a diode. The incident power is regulated either manually or automatically.

The measuring device according to the invention also comprises a detector 16 for detecting the microwave power P1(t) transmitted through the disturbed resonant cavity 4. Power P1(t) is linked with the properties of the impregnated fibre 3 passing through the cavity. Detector 16 can be constituted by a microwave contact diode or a Schottky diode, which can be coupled to the resonant cavity 4 with the aid of a flexible waveguide 18, more particularly constituted by a coaxial cable.

Detector 16 converts the power P1(t) transmitted by the ultra-high frequency cavity into an electric signal of the same frequency and the same amplitude. This electric signal is then filtered with the aid of a filter 20, e.g. formed by a circuit RC having a time constant $\tau$ of 1 second. The mean continuous signal $\overline{Vm}$ obtained at the output of filter 20 is consequently the convolution of the power P1(t) transmitted at resonance by the cavity 4 disturbed by the filtering function F(t).

The use of a sawtooth supply voltage of source 2 leads to the obtaining of a signal P1(t)t from the resonant cavity 4 and then a signal P2(t), as a function of time, such as shown in FIG. 2, which time-averaged over a second with the aid of filter 20 gives the continuous or d.c. voltage $\overline{Vm}$. The mean continuous signal $\overline{Vm}$ is then amplified with the aid of an amplifier 22 and supplied to an analog-digital converter 24 for processing by a microcomputer or microprocessor 26 of the MOTOROLA 6800 type.

Microprocessor 26 compares the value of the d.c. voltage $\overline{Vm}'$ from converter 24 with a calibration table located in a REPROM 28 and commands data capture every second. This calibration table is drawn up on the basis of a curve giving the variations of the d.c. voltage $\overline{Vm}'$ from converter 28, as a function of the impregnation rate T by resin of a fiber 3, which may or may not conduct electricity and which passes through the ultra-high frequency cavity 4.

This calibration curve is a function of the different elements of the measuring device. Furthermore, any modification of a particular element requires a new calibration.

The impregnation rate T determined in this way by the microprocessor 26 must be displayed in real time on a display screen 32 connected to the microprocessor 26 and supplied in parallel to a digital-analog converter 34 supplying an analog signal, which can e.g. be used for the control of the system of impregnating fibres by the resin, in order to ensure a homogeneous impregnation of the fibers, as a function of their subsequent use.

According to the invention, the ultra-high frequency cavity 4 must be usable with either conductive or non-conductive fibers and therefore in situations where the electric microwave field in the cavity can be either parallel or perpendicular to the fibers 3 passing through it.

For this purpose, the inventive cavity and as shown in FIG. 3, is a cylindrical cavity with a circular base, whereof the revolution axis 36 is oriented parallel to the direction x of the orthonormalized reference or coordinate xyz. In order to ensure that the temperature variations of the environment do not lead to modifications in the resonant frequency of cavity 4, the latter is made from Invar (an alloy of iron and nickel), with a silver or copper coating in order to obtain a good empty quality factor Qo at least equal to 1000.

Cavity 4 is centrally provided with a passage 38 for fiber 3, whose resin impregnation rate is to be measured. Passage 38 is rectilinear and oriented parallel to the direction Y of the orthonormalized reference, in accordance with one diameter of the cavity 4. This passage, which completely traverses the cavity, has in section the shape of a circle or a flattened ellipse as a function of the shape of the fiber to be controlled. In the case of a plate to be controlled of a few tenths of a mm and 3 mm wide, the elliptical passage can have a thickness of 3 mm and a widthh of 5 mm. There is a single fiber passage 38 and this can be used both for conductive fibers and for non-conductive fibers.

A mechanical system, not shown of the stretching roller type, makes it possible to maintain fiber 3 under tension, while also guiding it in passage 38.

Cavity 4 is also provided with a first microwave inlet e1 shaped like a cylindrical hole, thereof the revolution axis is parallel to direction z of reference xyz. Inlet e1 is coupled via the waveguide 6 to the microwave source 2. Associated with said first inlet e1 is an outlet s1, which is shaped like a cylinder, whereof the revolution axis is oriented according to axis z of reference xyz, said outlet being coupled via the waveguide 18 to the power detector 16.

Moreover, cavity 4 has a second inlet e2 and a second outlet s2 with a cylindrical shape, whereof the axes of revolution are parallel to axis y of the reference xyz, inlet e2 being coupled to the microwave source 2 via waveguide 6 and outlet s2 to detector 16 via waveguide 18.

The coupling of inlets e1, e2 and outlets s1, s2 respectively to waveguides 6 and 18 is ensured with the aid of four standard coaxial bases 40 of the microwave SMA type.

According to the invention, cavity 4 functions on resonant mode $TE_{113}$. Inlets e1 and e2, as well as outlets s1 and s2 are placed, as illustrated in parts A and B of FIG. 4, at a maximum of the electric field of the resonant mode on either side of passage 38, i.e., at 1/6 of the cavity length L.

Moreover, the cavity is provided with a mode filter 40 (FIGS. 3 and 4) constituted by a rectilinear, diameter 1 mm silver or copper wire, whose penetration length 1 in cavity 4 is equal to the radius of the latter. Said mode filter is oriented in accordance with direction z of reference xyz and is placed at a maximum of the resonant electric field, i.e. either facing inlet e1, or facing outlet s1.

When the fiber 3 to be investigated is conductive, e.g. of carbon or Kevlar, the inlet e1 and outlet s1 are respectively coupled to the microwave source 2 and detector 16. Conductive fiber 3, as indicated in parts A and C of FIG. 4, is then oriented perpendicular to component $\vec{E1}$ of the electric field of resonant mode $TE_{113}$, oriented in accordance with axis z, the component $\vec{E2}$ of this field oriented in direction y then being absorbed by the conductive fiber 3.

In the case of a non-conductive fiber, inlet e2 and outlet s2 are used. As indicated in parts B and D of FIG. 4, the non-conductive fiber is then oriented parallel to component $\vec{E2}$ of the electric field of resonant mode $TE_{113}$. The undesirable polarization $\vec{E1}$ of the electric field is then eliminated from the cavity with the aid of the mode filter 40.

FIG. 5 gives the resonance curves of the microwave cavity. Curve I corresponds to the resonance of the empty cavity, the empty resonance frequency Fo being close to 9450 MHz and curve II, displaced with respect to curve I, corresponds to the resonance of the cavity disturbed by the introduction into it of a fiber, whose resin impregnation rate is to be measured. The frequency shift is dependent on the type of fibers and the conditions of use.

The resonant frequency F1 of the disturbed cavity, as well as the microwave power P1(t) transmitted by the cavity are directly linked with the nature of the fiber (conductive or non-conductive), as well as its resin impregnation rate. The relations between F1, P1(t) and the impregnation rate T of the fibers are give in FR-A-2 556 470.

According to the invention, the frequency stability of the microwave source 2 is obtained by modulation of the emission frequency of said source around frequency F1 on a range of $\Delta 2F$, which must be large compared with the mid-height width $\Delta 1F$ of the resonance peak of the disturbed cavity and at least five times larger. Coefficient $\Delta 1F$ is defined by the ratio of F1/Q1, Q1 being the quality factor of the disturbed cavity.

In order to meet industrial requirements concerning the manufacture of composite materials with the aid of preimpregnated resin fibers, a device has been produced able to carry out mixed measurements of the resin impregnation rate with respect to parallelepipedic, 3 to 4 mm wide, 0.5 mm thick Kevlar and carbon fibers. The preimpregnated fibers 3 travel at a continuous speed of 4 m/minue. The latter does not influence the result of the measurement, so that it is possible to use the device according to the invention at much higher speeds, e.g. up to 60 m/min, provided that the positioning of the fiber is controlled.

The modulation of the supply voltage 2 was carried out with a frequency of 150 Hz applied to the varactor in such a way that source 2 operates on a range $\Delta 1F$ of 50 MHz, which is not critical, about the resonant frequency F1 of the cavity of close to 9400 MHz. The cavity, which is made from UZ10, has a diameter of 27 mm and a length L of 65 mm. Its empty quality factor is approximately 1000.

Fiber tensioning means are provided for stabilizing the position of the fiber in the cavity.

The processing system according to the invention has made it possible to display a mean value of 16 measurements of $\overline{Vm}$ or more precisely $\overline{V'm}$, corresponding to a passage of 1 m of impregnated fiber through the cavity. This mean measurement on 16 values has made it possible to carry out a comparison with a measurement of the impregnation rate T carried out by weighing the same fiber length (e.g. 1 to 10 meters). This correlation has made it possible to carry out the calibration of the processing system and to draw up the comparison table stored in the REPROM memory.

This system has made it possible to measure resin impregnation rates of 20 to 40% with an accuracy of $\pm 1\%$ on carbon fibers and $\pm 0.5\%$ on Kevlar fibers.

According to the type of application used, the measuring principle, the source-detection means and the measurement processing system remaining the same, with the exception of the resonant and exciting frequencies of the cavity. Only the dimensions of the ultra-high frequency cavity and the shape of the passage 38 are modified as a function of the shape or nature of the product to be controlled. The cavity exciting frequencies can be S, X or even Ku bands, the S band corresponding to frequencies between 2 and 4 GHz and the Ku band to frequencies between 12.4 and 18 GHz.

We claim:

1. Device for the continuous measurement of the impregnation rate by any substance of fiber (3), having a microwave source (2), a resonant cavity (4) adapted to be coupled to the microwave source via a first waveguide (6), the cavity having an axis of symmetry (36) parallel to a first direction (x) and a passage (38) for the fiber, traversing the cavity in its centre and oriented parallel to a second direction (6) perpendicular to the first direction, a detector (16) of the microwave power (P1(t)) transmitted by the cavity (4) and adapted to be coupled to the cavity via a second waveguide (18) and transforming said power into an electric signal, means (20, 22, 24, 26, 28) for processing the electric signal in order to deduce therefrom the impregnation rate and means (32) for displaying the impregnation rate, characterized in that the cavity (4) has a circular section excited in accordance with a resonant mode $TE_{11n}$, with n being an uneven number exceeding 1, said cavity having (a) a first input (e1) and a first output (s1) for microwaves, oriented parallel to a third direction (z) perpendicular to the first and second directions (x,y), said first input and output (e1, s1) being respectively connected to the first (16) and second (18) guides when the fiber (3) is conductive, so that the first component ($\vec{E1}$) of the electric field of the resonant mode $TE_{11n}$, oriented in the third direction (z) is perpendicular to the conductive fiber (3), (b) a second input (e2) and a second output (s2) for microwaves, oriented parallel to the second direction (y), said second input and output being respectively connected to the first (16) and second (18) guides when the fiber (3) is non-conductive, so that the second component ($\vec{E2}$) of the electric field of the resonant mode $TE_{11n}$, oriented in the second direction (x) is parallel to the non-conductive fiber and (c) a mode filter (40) for eliminating from the resonant cavity (4) said first component ($\vec{E1}$) of the electric field when the fiber (3) is non-conductive.

2. Device according to claim 1, characterized in that the mode filter (40) is constituted by a rigid conductive wire penetrating cavity (4) and oriented in the third direction (z).

3. Device according to claims 1 or 2, characterized in that the mode filter (40) is located at an antinode of the first component ($\vec{E1}$) of the electric field.

4. Device according to claim 1, characterized in that the penetration of mode filter (40) into cavity (4) is close to the radius of the cavity.

5. Device according to claim 1, characterized in that the outer surface of mode filter (40) is coated with a good electricity conducting metal.

6. Device according to claim 1, characterized in that the walls of the cavity (4) are provided with a good electricity conducting metal.

7. Device according to claim 1, characterized in that frequency stabilization means (5) for microwave source (2) are provided.

8. Device according to claim 7, characterized in that the stabilization means (5) incorporate a sawtooth voltage generator modulating the frequency of source ((2) about the resonant frequency (F1) of the disturbed cavity (4) over a frequency range which is large compared with the mid-height width ($\Delta 1F$) of the peak of the resonance curve giving the microwave power (P1(t)) transmitted by the disturbed cavity as a function of the exciting frequency of the cavity.

9. Device according to claim 1, characterized in that the processing means incorporate an electronic circuit (20) converting the signal emitted by detector (18) into a continuous mean signal, an amplifier (22) for amplifying said continuous mean signal, an analog-digital converter (24) for converting the amplified signal and means (26, 28) for converting the digital signal from the converter into an impregnation rate.

* * * * *

UNITED STATES PATENT AND TRADEMARK OFFICE
CERTIFICATE OF CORRECTION

PATENT NO. : 4,885,527

DATED : December 5, 1989

INVENTOR(S) : Lacombe et al.

It is certified that error appears in the above-identified patent and that said Letters Patent is hereby corrected as shown below:

Column 1, line 13, delete "applied" and insert --applies--.

Column 1, line 19, after "parts" insert --employed more particularly in the car, aeronautical and space fields.--

Column 2, line 9, delete "are" and insert --as--.

Column 2, line 11, delete "interger" and insert --integer--.

Column 2, line 34, delete "on" (second occurrence) and insert --or--.

Column 2, line 35, afters "fibers" insert --,--.

Column 2, line 43, after "substance" insert --,--.

Column 5, line 59, delete "of" and insert --for--.

Column 6, line 48, delete "widthh" and insert --width--.

Column 6, line 51, after "shown" insert --,--.

Column 6, line 55, delete "thereof" and insert --whereof--.

Column 7, line 49, delete "give" and insert --given--.

UNITED STATES PATENT AND TRADEMARK OFFICE
CERTIFICATE OF CORRECTION

PATENT NO. : 4,885,527

DATED : December 5, 1989

INVENTOR(S) : Lacombe et al

It is certified that error appears in the above-identified patent and that said Letters Patent is hereby corrected as shown below:

Column 8, line 3, after "voltage" insert --of source--.

Signed and Sealed this

Nineteenth Day of November, 1991

*Attest:*

HARRY F. MANBECK, JR.

*Attesting Officer*  *Commissioner of Patents and Trademarks*